United States Patent [19]

Geary et al.

[11] Patent Number: 5,505,967
[45] Date of Patent: Apr. 9, 1996

[54] MICROPARTICULATE PHARMACEUTICAL DELIVERY SYSTEM

[75] Inventors: Richard S. Geary; Herman W. Schlameus, both of San Antonio, Tex.

[73] Assignee: Southwest Research Institute, San Antonio, Tex.

[21] Appl. No.: 339,416

[22] Filed: Nov. 14, 1994

Related U.S. Application Data

[62] Division of Ser. No. 36,633, Mar. 24, 1993, Pat. No. 5,382,435.

[51] Int. Cl.$^6$ .............................. A61K 9/16; A61K 9/20; A61K 9/28; A61K 9/48

[52] U.S. Cl. .................. 424/497; 424/450; 424/451; 424/464; 424/469; 424/474; 424/479; 424/482; 424/493; 424/494; 424/495; 428/402.21; 428/402.24; 428/403; 264/4.3; 264/4.6; 514/772.3; 514/779; 514/781; 514/785; 514/962; 514/963

[58] Field of Search ................. 424/450, 451, 424/464, 469, 474, 490, 493, 494, 495, 497, 479, 482; 428/402.2, 402.21, 402.24, 403; 436/829; 264/4.3, 4.32, 4.33, 4.6; 514/962, 963, 772.3, 777, 779, 781, 785

[56] References Cited

U.S. PATENT DOCUMENTS

| | | | |
|---|---|---|---|
| 4,525,339 | 6/1985 | Behl et al. | 424/494 |
| 5,026,559 | 6/1991 | Eichel et al. | 424/490 |
| 5,171,580 | 12/1992 | Iamartino et al. | 424/490 |

*Primary Examiner*—Carlos A. Azpuru
*Attorney, Agent, or Firm*—John L. Sigalos

[57] ABSTRACT

A pharmaceutical composition comprising a shaped enteric material having distributed therethrough preferably substantially uniformly, pharmaceutical loaded particles, said particles having a size no greater than about 10 microns in any dimension and being alkali insoluble and the method of delivering pharmaceuticals to Peyer's glands.

6 Claims, 1 Drawing Sheet

MICROPARTICULATE PHARMACEUTICAL DELIVERY SYSTEM

This application is a division of application Ser. No. 08/036,633, filed Mar. 24, 1993, now U.S. Pat. No. 5,382,435.

BACKGROUND OF THE INVENTION

The present invention relates to a microparticulate pharmaceutical delivery system which is capable of ensuring that the pharmaceutical to be delivered can be directed to be absorbed in the Peyer's glands of the small intestine.

There are a number of enteric coatings which are utilized to ensure that acid labile pharmaceuticals or other materials can get safely by the acidic pH conditions in the stomach when ingested orally and which are dissolved in the alkaline pH conditions of the intestine and absorbed therein. However, there are many drugs in which it is desired to avoid exposure to both the acidic conditions of the stomach and the akaline conditions of the intestine and yet be absorbed in the intestine so they can be given in oral dosage form. Many pharmaceuticals are labile, inactivated or in same manner have their effectiveness limited in whole or in part, under the pH conditions existing in the stomach and intestine.

It is known that the small intestine comprises three main sections, the duodenum, jejunum, and the ileum. Located primarily in the ileum are Peyer's glands, often referred to as "Peyer's patches", which contain phagocytic cells which act to capture solid particles of ten microns or less that come into the intestine. This is important since particles cannot otherwise pass through the intestinal lining.

Some Peyer's glands exist in the jejunum particularly in the lower portion thereof as one comes to the ileum, but they are few in number and most are located in the ileum. Occasionally, and rarely, some are seen in the duodenum.

Heretofore, a satisfactory procedure to give oral doses of pharmaceuticals for delivery to the Peyer's patch that are acid and akali labile has not been available.

SUMMARY OF THE INVENTION

The present invention overcomes the deficiencies of orally administered acid and akali labile pharmaceutical compositions and provides an orally administered product which can be readily adsorbed only in the Peyer's glands present in the small intestine.

Briefly stated, the present invention comprises a pharmaceutical composition comprising a shaped enteric material having distributed substantially uniformly therethrough pharmaceutical-loaded particles, said particles having a size no greater than about 10 microns in any dimension and being alkali insoluble and the method of delivering pharmaceuticals to Peyer's glands.

DETAILED DISCUSSION

Figure 1:
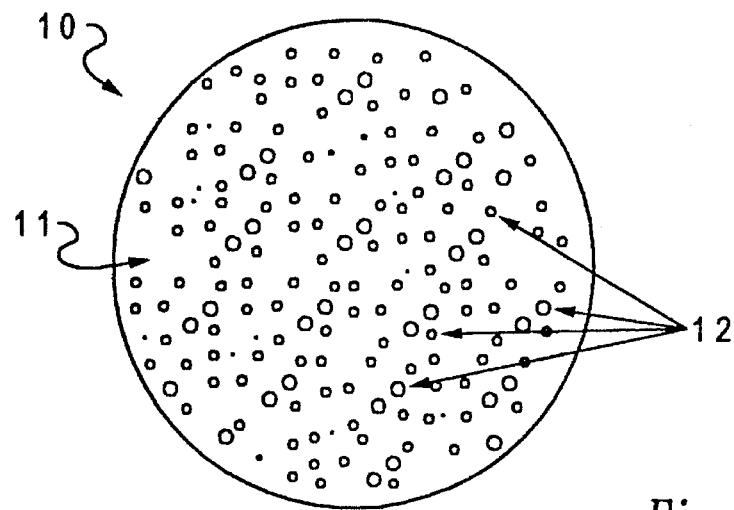
FIG. 1 shows a pharmaceutical composition in accord with the instant invention in the form of beads containing pharmaceutical-loaded microparticles.

It will be seen that the two essentials of the instant invention are a shaped enteric material and the pharmaceutical-loaded particles distributed therethrough.

As used therein the phrase "shaped enteric material" means any material known to those in the pharmaceutical art to be able to resist dissolution under the acidic conditions present in the stomach and yet be dissolved in the alkaline conditions that prevail in the small intestine. These materials are well known and include alginates, alkali-soluble acrylic resins (EUDRAGITS®), cellulose acetate phthalate, hydroxypropyl methylcellulose phthalate, and the like. The term "shaped" as part of the expression simply means that the material can be in the form of beads or other shapes commonly used in forming pharmaceutical compositions. The size of the shaped enteric material is not critical, but, ordinarily for ease of ingestion they should be the smallest size possible ensuring that they will safely conduct the pharameutical-loaded particles therein through the stomach and into the intestine. It has been found that it is desired to primarily have beads of approximately 2 mm to 6 mm in size, preferably around 4 millimeters is diameter. The individual shaped material, such as beads, can be incorporated into conventional gelatin capsules or other like means for oral use. The beads, loaded with the particles can also be included in suitable conventional pharmaceutically-acceptable liquid. bases for oral administration.

With respect to the pharamceutical-loaded particles, they are composed of an alkali insoluble encapulating substance and the active pharmaceutical itself and are 10 microns or less in size. The term "particles" as used in this invention is meant to include nanocapsules, microcapsules, nanospheres, microspheres, liposomes, and the like, in which the particles can be made of a cellulosic material such as ethylcellulose, a polylactide, a polylactide-co-glycolide, or polycaprolactone, a liposome, an emulsified oil or fat, a gelatin, albumin, an acrylic resin, and the like, all conventional and well known alkali-insoluble encapsulating materials.

As to the pharmaceutical loaded in the particles there can be used any acid and alkali labile products such as peptides, proteins, synthetic drugs, oral vaccines, and the like, although the instant composition is especially well suited for biotechnology recombinant protein products and oral vaccines which require protection not only in the stomach, but also in the intestinal tract.

It is important that in the production of the pharmaceutical compositions of the instant invention that no heat be utilized since the same can have a deleterious effect on the pharmaceuticals noted, especially on the fragile recombinant products such as the protein products and the oral vaccines.

It will be evident that the amount of active pharmaceutical in the particles can vary greatly, dependent mainly on the dosage desired to be given. For any given composition the proper dosage amount is determined by including the requisite number of particles in the composition formed by admixing the particles with the shaped enteric material and including the proper amount of the composition in the oral medicament; e.g. gelatin capsule.

The preparation of the pharmaceutical composition of the instant invention will be described in conjunction with the preferred shaped enteric material, namely an alginic acid.

What first transpires is the preparation of the particles in the form of nanocapsules, microcapsules, nanospheres, and the like, and these capsules can be prepared by any conventional encapsulation process, preferably one that does not utilize any heat. Conventional encapsulation processes such as solvent evaporation, coacervation/phase separation, emulsion polymerization, emulsion extraction, and aerosol generation can be used to prepare the small drug-loaded particles. The particulars (apparatus, and the like) of these processes are known to those experienced in the art of microencapsulation and need no further elaboration here. Any process than can be used to prepare capsules less than 10 microns, preferably without the use of heat, can be used to prepare the small particles. The encapsulation is carried out to ensure that the resultant particles are no more than about 10 microns in diameter.

The pharmaceutical-loaded particles are then dispersed into a solution of sodium alginate in water and the beads form simply by adding the mixture dropwise to an acidic solution, such as citric acid, which will immediately insolubilize the sodium alginate drop into the shape of a bead. The beads thus formed can be removed from the solution and dried until used. The beads will remain intact under ambient conditions and when administered for ingestion they remain intact at the pH encounted in the stomach. The alginic acid beads release the pharmaceutical-loaded particles in the intestinal tract for absorption by the phagocytic cells of the Peyer's glands.

Reference to FIG. 1 of the drawing shows such a bead 10 comprising the enteric shaped material 11, (alginic acid) having dispersed uniformly therethrough the pharmaceutical-loaded particles 12 having a variety of particle sizes, if desired, but in any event none greater than 10 microns in diameter. It will be understood that in those situations where it is desired to have in the same bead or other shaped enteric material not only a pharmaceutical to be delivered to the Peyer's glands, but also any pharmaceutical(s) not alkali labile in the intestinal tract can be incorporated in the alginate and can be of a diameter larger than 10 microns. It will be also evident that different shaped particles and particles loaded with different pharmaceuticals can be incorporated in the same bead.

Figure 2:
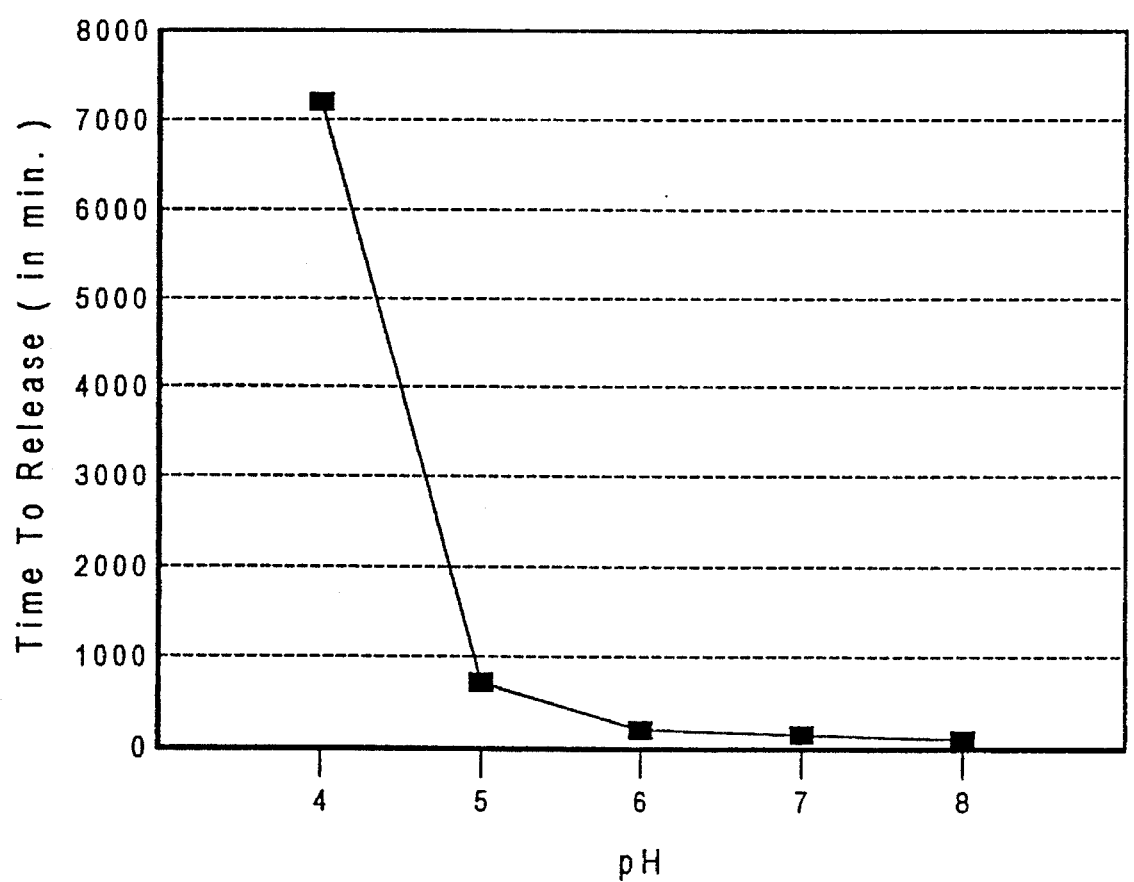
FIG. 2 is a graph depicting the dissolution pH response of a pharmaceutical composition in accord with the present invention.

FIG. 2 is a graph depicting the time, in minutes, within which 100% of the enteric material will be dissolved at various pH levels. It shows the almost instantaneous dissolution at pH 8 which would leave the particles free to be absorbed by the phagocytic cells in the Peyer's glands.

The invention will be further described in connection with the following example which is set forth for purposes of illustration only.

EXAMPLE

Albumin, to simulate a pharmaceutical agent, was encapsulated with polylactide-co-glycolide utilizing a solvent evaporation process that did not involve heating to form microcapsules no greater than 10 microns in diameter. The prepared microcapsules were substantially uniformly dispersed into a solution prepared by dissolving sodium alginate in deionized water.

Beads of the mixture were formed by adding the mixture dropwise to an aqueous citric acid solution. The result is that the alginic acid insolubilizes forming beads containing the pharmaceutical-loaded particles dispersed substantially uniformly therethrough.

Beads of approximately 4 mm in diameter were prepared.

In order to determine the dissolution profile, beads were exposed to buffers at various pHs giving the following dissolution profile:

pH 2: No release at 12 hours
pH 3: No release at 12 hours
pH 4: Approx. 10% release at 12 hours
pH 5: 100% at 12 hours
pH 6: 100% at 105 minutes
pH 7: 100% at 65 minutes
pH 8: 100% at 50 minutes It will be evident that in place of the sodium alginate other conventional enteric materials as discussed above may be utilized and equally any pharmaceuticals can be utilized. What is critical, however, is that the pharmaceutical loaded-particles, preferably in the shape of a microcapsule or microsphere, be no larger than about 10 microns in diameter and that the encapsulating material be alkali-insoluble.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. The method of delivering a pharmaceutical to be absorbed in Peyer's glands comprising loading said pharmaceutical into an alkali-insoluble particle having a maximum size in any dimension no greater than about 10 microns, incorporating said particle in a shaped enteric material, and administering said material.

2. The method of claim 1 wherein the enteric material is an alginate, alkali-soluble acrylic resin, cellulose acetate phthalate, hydroxypropyl methylcellulose phthalate, or mixtures thereof.

3. The method of claim 2 wherein the particle containing the pharmaceutical is made of an alkali-insoluble cellulosic material, a polylactide, a polylactide-co-glycolide, a polycaprolactone, a liposome, an emulsified oil or fat, a gelatin, an albumin, an acrylic resin, or mixtures thereof.

4. The method of claim 3 wherein the shaped enteric material is in the form of a bead having a diameter of about 2 to 6 mm.

5. The method of claim 4 wherein the enteric material is an alginate and the particles are made of ethylcellulose.

6. The method of claim 5 wherein the particles are in the form of nanocapsules, microcapsules, nanospheres, microspheres, liposomes, or mixtures thereof.

* * * * *